(12) United States Patent
Jiao et al.

(10) Patent No.: US 11,773,435 B2
(45) Date of Patent: Oct. 3, 2023

(54) METHOD FOR CAPTURING ANCIENT DNA OF WOODEN CULTURAL RELIC

(71) Applicant: Research Institute of Wood Industry, Chinese Academy of Forestry, Beijing (CN)

(72) Inventors: Lichao Jiao, Beijing (CN); Yafang Yin, Beijing (CN); Yang Lu, Beijing (CN); Juan Guo, Beijing (CN); Yu Guo, Beijing (CN); Tuo He, Beijing (CN); Lingyu Ma, Beijing (CN)

(73) Assignee: RESEARCH INSTITUTE OF WOOD INDUSTRY, CHINESE ACADEMY OF FORESTRY, Beijing (CN)

( * ) Notice: Subject to any disclaimer, the term of this patent is extended or adjusted under 35 U.S.C. 154(b) by 0 days.

(21) Appl. No.: 18/111,604

(22) Filed: Feb. 20, 2023

(65) Prior Publication Data

US 2023/0265494 A1   Aug. 24, 2023

(30) Foreign Application Priority Data

Feb. 18, 2022 (CN) .......................... 202210149079.9

(51) Int. Cl.
*C12Q 1/686* (2018.01)
*C12N 15/10* (2006.01)

(52) U.S. Cl.
CPC .......... *C12Q 1/686* (2013.01); *C12N 15/1093* (2013.01)

(58) Field of Classification Search
CPC .... C12Q 1/686; C12Q 1/6806; C12Q 1/6895; C12Q 2523/313; C12Q 2600/13; C12N 15/1093
See application file for complete search history.

(56) References Cited

PUBLICATIONS

Lendvay et al. Improved recovery of ancient DNA from subfossil wood—application to the world's oldest Late Glacial pine forest. New Phytologist (2018) 217:1737-1748. (Year: 2018).*
Akhmetzyanov et al. DNA of centuries-old timber can reveal its origin. Nature Research (2020) 10:20316, pp. 1-10. (Year: 2020).*

* cited by examiner

*Primary Examiner* — David C Thomas
(74) *Attorney, Agent, or Firm* — Bayramoglu Law Offices LLC (57) ABSTRACT

A method for capturing ancient DNA of a wooden cultural relic, sequentially includes the following steps: sampling, removing exogenous DNA contamination on the inner part and the outer surface of a sample, and effectively obtaining the ancient DNA of the wooden cultural relic through vacuum freeze-drying dehydration, sample grinding, rinsing, cell lysis, DNA genome enrichment and hybridization and capturing. The method focuses on precise capture of the ancient DNA of the wood cells of the wood cultural relic, not only breaks through the problem that effective acquisition of the DNA of the wood cultural relic is difficult to realize by a conventional wood DNA extraction method, but also provides possibility for analysis and utilization of the ancient DNA with typical characteristics of serious exogenous contamination, low DNA content, high degradation, extensive damage and the like.

18 Claims, 1 Drawing Sheet

METHOD FOR CAPTURING ANCIENT DNA OF WOODEN CULTURAL RELIC

CROSS REFERENCE TO THE RELATED APPLICATIONS

This application is based upon and claims priority to Chinese Patent Application No. 202210149079.9, filed on Feb. 18, 2022, the entire contents of which are incorporated herein by reference.

TECHNICAL FIELD

The present invention belongs to fields of wood molecular archaeology, and particularly relates to a method capable of effectively capturing an ancient DNA of a wooden cultural relic.

BACKGROUND

The in-depth wood archaeological research has important theoretical and practical significance. Accurate identification of wood species is the premise of wood archaeological research and an important basis for understanding the natural and historical connotations of wooden remains. At present, wood species are generally identified based on wood anatomy, mainly through the combination of macroscopic and microscopic characteristics of the wood. However, based only on the characteristics of wood and its anatomical structure, only the "genus" or "class" of the wood, rather than the "species", can be identified. At the same time, the burial or preservation environment of wooden remains is an important factor affecting the anatomical structure and cell wall morphology of the wood. The degradation of the wood will be accelerated due to conditions such as microorganisms, humidity, pH and salt content in the environment, resulting in changes in the cell structure of the wood such as to holes, shrinkage or deformation behaviors. The severe loss or change in the cell structure characteristics of the wood has brought great difficulty to the anatomical identification.

In recent years, domestic and exogenous scholars have carried out wood species identification based on molecular biology methods, and have provided the traceability of information on rare and endangered wood species. The relatively closed space formed by wood cells due to the hard lignified cell wall provides a possible good environment for the long-term preservation of ancient DNA. However, under the joint action of time and space dimensions, the endogenous ancient DNA of archaeological wood will undergo significant changes such as degradation and damage.

Ancient sample may be susceptible to contamination by other organisms (bacteria, fungi, archaea) or modern DNA during preservation, resulting in a very low proportion of endogenous ancient DNA.

The problem of contamination by exogenous DNA makes the endogenous ancient DNA difficult to capture through conventional polymerase chain reaction (PCR reaction), or even impossible to be amplified.

SUMMARY

The object of the present invention is to provide a method for capturing an ancient DNA of a wooden cultural relic, which breaks through the conventional DNA extraction and PCR amplification methods that cannot achieve effective acquisition of the DNA information of the dry-state, particularly waterlogged archaeological wood, and lays the foundation for the scientific protection and restoration of the wooden cultural relic.

In order to solve the above technical problems, the present invention provides the following technical solutions.

The present invention provides a method for capturing an ancient DNA of a wooden cultural relic, comprising:
- step 100: cutting a wood sample with a volume V from the wooden cultural relic, and removing an exogenous DNA contamination from the wood sample, wherein
  a method for removing the exogenous DNA contamination of the wood sample sequentially involves with an ultraviolet irradiation, an outer surface removal, a soaking, and a washing,
  the ultraviolet irradiation is kept for 5-48 h under a radiation of 10-50 W,
  the outer surface removal is carried out by cutting off an outer surface of the wood sample by 1-4 mm using a sterile scalpel,
  the soaking is to soak the wood sample in a sodium hypochlorite solution containing a 0.01-0.10% Tween-20 with a mass fraction of 1-5% for 1-10 min,
  the washing is carried out using a double distilled water for 1-3 times, each time for 1-5 min;
- step 200: grinding the wood sample into a powder sample at a low temperature;
- step 300: rinsing the powder sample 2-3 times to obtain a rinsed powder sample, wherein
  a rinsing solution CB for rinsing the powder sample includes a 10-50 mM Tris-HCl at pH=8.0, a 5-20 mM EDTA at pH=8.0, a 5-10% PVP-40, a 5% glycerol, a 5-10% PEG8000, a 300-500 mM sorbitol, and a 50 mM DTT;
- step 400: sequentially carrying out a cell lysis, a DNA purification and a concentration on the rinsed powder sample to obtain and collect a sample genomic DNA;
- step 500: constructing a DNA library and designing an RNA probe based on the sample genomic DNA, and then hybridizing the RNA probe with the DNA library to form an RNA-DNA complex solution;
- step 600: capturing an RNA-DNA complex from the RNA-DNA complex solution using a streptavidin-labeled magnetic bead;
- step 700: washing the RNA-DNA complex to obtain a washed RNA-DNA complex, and then dissolving the washed RNA-DNA complex to obtain a target DNA product; and
- step 800: carrying out a PCR amplification on the target DNA product, and constructing a target DNA library for a high-throughput sequencing.

As a preferred technical solution of the present invention, if the wood sample is a sample from a waterlogged wooden cultural relic, before grinding the wood sample into the powder sample at the low temperature, carrying out a vacuum freeze drying and a dehydration on the wood sample from which the exogenous DNA contamination is removed.

As a preferred technical solution of the present invention, in a process of the vacuum freeze drying and the dehydration, the wood sample is pre-frozen in a −20° C. low-temperature refrigerator, and then transported to a freeze dryer to dry under a condition of −40° C., 0.5-2.0 kPa for 36-72 h for the dehydration.

As a preferred technical solution of the present invention, a method for grinding the wood sample into the powder sample at the low temperature in the step 200 involves with adding a cross-linked polyvinylpyrrolidone powder ½-1 a weight of the wood sample into a grinding tube, and grinding together under a low temperature environment of −196° C., making a powder mesh number not less than 200 mesh.

As a preferred technical solution of the present invention, the cell lysis in the step 400 involves with preheating a DNA lysis buffer LB to 55° C., adding the DNA lysis buffer LB to the powder sample, oscillating and mixing well to obtain a resulting mixture, and incubating the resulting mixture in a metal bath with an oscillation frequency of 1200 rpm at 50-65° C. for 5-12 h.

As a preferred technical solution of the present invention, the DNA purification in the step 400 involves with
- adding ⅕ volume of a DNA lysis buffer and a chloroform-isoamyl alcohol with a volume ratio of 24:1 to a first centrifuge tube, oscillating and mixing well through a vortex, mixing up and down for 10 min, centrifuging at 8500 g for 15 min to obtain a first supernatant, and transferring the first supernatant to a second centrifuge tube;
- adding the chloroform-isoamyl alcohol with the volume ratio of 24:1 in a same volume as that of the first supernatant, oscillating and mixing well through the vortex, centrifuging at 8500 g for 15 min to obtain a second supernatant, and transferring the second supernatant to a freshly sterilized centrifuge tube;
- adding a pre-cooled isopropanol in a same volume as a volume of the second supernatant, ⅕ volume of a 3M NaAC (PH=8.0), and 2-10 µl of glycogen, placing a resulting mixture at −20° C. for 1 h, centrifuging at 9000 g for 15 min, and discarding a resulting supernatant;
- adding 450 µl of a 70% ethanol solution to wash a precipitate, centrifuging at 8000 g for 10 min, discarding the supernatant, and placing the precipitate on a sterile operating table for drying; and
- adding the double distilled water to dissolve to obtain the crude DNA extract.

As a preferred technical solution of the present invention, if the crude DNA extract after a primary purification still has a dark color, carrying out a secondary purification on the crude DNA extract using a silicon spin column, wherein a method of the secondary purification involves with
- adding the crude DNA extract obtained by the primary purification to a binding buffer BB with a volume 10-15 times a volume of the crude DNA extract, and mixing up and down for 2-6 min,
- transferring a mixed solution to a silicon spin column combination tube, centrifuging at 2000 g for 10 min, and discarding a filtrate;
- centrifuging at 6000 g for 1 min, and drying the silicon spin column;
- adding 500-1000 µl of a washing buffer WB, centrifuging at 6000 g for 1 min, washing the silicon spin column, discarding a filtrate, and repeating twice;
- centrifuging at 8500 g for 1 min, and drying the silicon spin column; and
- transferring the silicon spin column to a DNA collection tube, adding 20-50 µl of a release buffer RB, incubating for 5-15 min, centrifuging at a maximum speed for 30 s, and repeating twice, thereby collecting a total of 50 µl of a DNA extract, wherein
- the binding buffer BB is composed of a 5 M guanidine hydrochloride, a 40% (v/v) isopropanol, a 0.05% Tween-20, and a 90 mM NaAC at pH=5.2;
- the washing buffer WB is composed of a 10 mM Tris-HCl at pH=7.5 and a 80% (v/v) ethanol;
- the release buffer RB is composed of a 100 mM Tris-HCl at pH=8.0, a 10 mM EDTA at pH=8.0 and a 0.05% Tween-20;
- the silicon spin column refers to a combined silicon spin column of a High Pure Extender Assembly of High Pure Viral Nucleic Acid Large Volume Kit (Roche Applied Science).

As a preferred technical solution of the present invention, the DNA lysis buffer LB is composed of a 2% (w/v) CTAB, a 10-50 mM Tris-HCl at pH=8.0, a 50-100 mM NaCl, a 10-20 mM CaCl$_2$, a 5-20 mM EDTA at pH=8.0, a 2.5 mM PTB, 4-6% (w/v) PVP-40, a 50-100 mM DTT and a 0.4-0.5 mg/mL proteinase K.

As a preferred technical solution of the present invention, the step 500 involves with
- starting a program of a PCR machine, placing a Buffer T1 at 95° C. for 3-5 min, sucking 3-10 µl and then immediately transferring to a first centrifuge tube;
- after placing a Buffer T2 at 65° C. for 3-5 min, sucking 5-15 µl and quickly transferring to the first new centrifuge tube;
- after placing a Buffer T3 at 65° C. for 1-5 min, sucking 3-10 µl and quickly transferring to the first centrifuge tube;
- using a pipette to mix well, sealing a cap of the first centrifuge tube, and hybridizing for 12-48 h, wherein
- the Buffer T1 is composed of a 1 µg/µL human Cot-1 DNA, a 1 µg/µL salmon sperm DNA, a MYcroarray blocker and a DNA library at a volume ratio of (2-5):(1-4):1:(2-8);
- the Buffer T2 is composed of a 0.5 M EDTA, a 20×SSPE buffer, a 50×Denhardt's solution and a 1% SDS at a volume ratio of 1:(10-35): (5-15): (5-12);
- the Buffer T3 is composed of a 10 mg/mL yeast tRNA, a RNase inhibitor and a biotinylated RNA probe at a volume ratio of (3-12):1:(0-2.0).

As a preferred technical solution of the present invention, the step 600 involves with
- adding a hybridized solution to a centrifuge tube containing a Buffer T4 and a magnetic bead;
- incubating the hybridized solution on a rotator at a room temperature for 0.5-2.5 h; and
- placing a centrifuge tube containing the magnetic bead on a magnetic stand, standing for 3-8 min, and discarding a supernatant, wherein
- the Buffer T4 is composed of a 1M NaCl, a 10 mM Tris-HCl and a 1 mM EDTA at pH=7.5.

As a preferred technical solution of the present invention, the step 700 involves with
- adding 50-300 µL of a Wash Buffer #1 to a second centrifuge tube containing a magnetic bead and mixing through a vortex;
- incubating at a room temperature for 5-20 min, and stirring every 3 min;
- spinning the second centrifuge tube downward;
- placing the second centrifuge tube containing the magnetic bead on a magnetic stand, standing for 1-10 min, and then discarding a supernatant;
- adding 50-220 µL of a Wash Buffer #2 to the second centrifuge tube containing the magnetic bead, and mixing through the vortex;
- applying a water bath to the magnetic bead and the Wash Buffer #2 at 65° C. for 5-15 min, and stirring once every 2 min;

placing the second centrifuge tube containing the magnetic bead on the magnetic stand, standing for 1-10 min, discarding a supernatant, and repeat twice, wherein the Wash Buffer #1 is composed of a 1×SSC buffer and a 0.05-0.2% SDS buffer, the Wash Buffer #2 is composed of a 0.1×SSC buffer and a 0.05-0.2% SDS buffer, gently removing a residual liquid from the magnetic bead, and eluting with 30-100 μL of a TET buffer to obtain a target DNA solution, wherein the TET buffer is composed of a 10 mM Tris-HCl and a 0.005% Tween 20.

As a preferred technical solution of the present invention, the step 800 involves with carrying out a Post-PCR amplification on the target DNA solution to construct a DNA library, wherein a reaction system of the PCR amplification is composed of a KAPA Taq HotStart Mix, a Illumina IS5 primer, a Illumina IS6 primer, a DNA and a double distilled water at a volume ratio of (10-50):1:1:(12-25):(3-15);

reaction procedures of the PCR amplification include a pre-denaturation at 94-96° C. for 0.5-10 min, a denaturation at 94-96° C. for 0.1-2 min, an annealing at 40-65° C. for 0.1-2 min, an extension at 72° C. for 0.5-2 min, cycling 20-50 times, and a final extension at 72° C. for 2-15 min.

As a preferred technical solution of the present invention, a method for grinding the wood sample into the powder sample at the low temperature in the step 200 involves with adding a cross-linked polyvinylpyrrolidone powder ½-1 a weight of the wood sample into a grinding tube, and grinding together under a low temperature environment of −196° C., making a powder mesh number not less than 200 mesh.

As a preferred technical solution of the present invention, the cell lysis in the step 400 involves with preheating a DNA lysis buffer LB to 55° C., adding the DNA lysis buffer LB to the powder sample, oscillating and mixing well to obtain a resulting mixture, and incubating the resulting mixture in a metal bath with an oscillation frequency of 1200 rpm at 50-65° C. for 5-12 h.

As a preferred technical solution of the present invention, the DNA purification in the step 400 involves with adding ⅕ volume of a DNA lysis buffer and a chloroform-isoamyl alcohol with a volume ratio of 24:1 to a first centrifuge tube, oscillating and mixing well through a vortex, mixing up and down for 10 min, centrifuging at 8500 g for 15 min to obtain a first supernatant, and transferring the first supernatant to a second centrifuge tube;

adding the chloroform-isoamyl alcohol with the volume ratio of 24:1 in a same volume as that of the first supernatant, oscillating and mixing well through the vortex, centrifuging at 8500 g for 15 min to obtain a second supernatant, and transferring the second supernatant to a freshly sterilized centrifuge tube;

adding a pre-cooled isopropanol in a same volume as a volume of the second supernatant, ⅕ volume of a 3M NaAC (PH=8.0), and 2-10 μl of glycogen, placing a resulting mixture at −20° C. for 1 h, centrifuging at 9000 g for 15 min, and discarding a resulting supernatant;

adding 450 μl of a 70% ethanol solution to wash a precipitate, centrifuging at 8000 g for 10 min, discarding the supernatant, and placing the precipitate on a sterile operating table for drying; and adding the double distilled water to dissolve to obtain a crude DNA extract.

As a preferred technical solution of the present invention, if a crude DNA extract after a primary purification still has a dark color, carrying out a secondary purification on the crude DNA extract using a silicon spin column, wherein a method of the secondary purification involves with adding the crude DNA extract obtained by the primary purification to a binding buffer BB with a volume 10-15 times a volume of the crude DNA extract, and mixing up and down for 2-6 min;

transferring a mixed solution to a silicon spin column combination tube, centrifuging at 2000 g for 10 min, and discarding a filtrate;

centrifuging at 6000 g for 1 min, and drying the silicon spin column;

transferring the silicon spin column to a DNA collection tube, adding 20-50 μl of a release buffer RB, incubating for 5-15 min, centrifuging at a maximum speed for 30 s, and repeating twice, thereby collecting a total of 50 μl of a DNA extract, wherein the binding buffer BB is composed of a 5 M guanidine hydrochloride, a 40% (v/v) isopropanol, a 0.05% Tween-20, and a 90 mM NaAC at pH=5.2;

the washing buffer WB is composed of a 10 mM Tris-HCl at pH=7.5 and a 80% (v/v) ethanol;

the release buffer RB is composed of a 100 mM Tris-HCl at pH=8.0, a 10 mM EDTA at pH=8.0, and a 0.05% Tween-20;

the silicon spin column refers to a combined silicon spin column of a High Pure Extender Assembly of High Pure Viral Nucleic Acid Large Volume Kit (Roche Applied Science).

As a preferred technical solution of the present invention, the step 500 involves with starting a program of a PCR machine, placing a Buffer T1 at 95° C. for 3-5 min, sucking 3-10 μl and then immediately transferring to a first centrifuge tube;

after placing a Buffer T2 at 65° C. for 3-5 min, sucking 5-15 μl and quickly transferring to the first centrifuge tube;

after placing a Buffer T3 at 65° C. for 1-5 min, sucking 3-10 μl and quickly transferring to the first centrifuge tube;

using a pipette to mix well, sealing a cap of the first centrifuge tube, and hybridizing for 12-48 h, wherein the Buffer T1 is composed of a 1 μg/μL human Cot-1 DNA, a 1 μg/L salmon sperm DNA, a MYcroarray blocker, and the DNA library at a volume ratio of (2-5):(1-4):1:(2-8);

the Buffer T2 is composed of a 0.5 M EDTA, a 20×SSPE buffer, a 50×Denhardt's solution, and a 1% SDS at a volume ratio of 1:(10-35):(5-15):(5-12);

the Buffer T3 is composed of a 10 mg/mL yeast tRNA, a RNase inhibitor, and a biotinylated RNA probe at a volume ratio of (3-12):1:(0-2.0).

As a preferred technical solution of the present invention, the step 600 involves with adding a hybridized solution to a centrifuge tube containing a Buffer T4 and a magnetic bead;

incubating the hybridized solution on a rotator at a room temperature for 0.5-2.5 h; and placing a centrifuge tube containing the magnetic bead on a magnetic stand, standing for 3-8 min, and discarding a supernatant, wherein the Buffer T4 is composed of a 1M NaCl, a 10 mM Tris-HCl, and 1 mM EDTA at pH=7.5.

Compared with the conventional techniques, the present invention has the following beneficial effects.

The present invention provides the method for capturing ancient DNA of wooden cultural relic, which includes sample pretreatment, wood cell lysis, ancient DNA genome enrichment, hybrid capture, etc. By removing the exogenous DNA contamination existing at the inner part or outer surface of the sample, and carrying out vacuum freeze drying and dehydration, sample grinding, rinsing and other treatment measures during the pretreatment process of the sample, the present invention can solve the problems that the endogenous ancient DNA is difficult to capture through conventional polymerase chain reaction (PCR reaction), or even impossible to be amplified, which breaks through the technical bottleneck of the conventional wood DNA extraction and PCR amplification methods.

BRIEF DESCRIPTION OF THE DRAWINGS

In order to clearly illustrate the embodiments of the present invention or the technical solutions in the conventional techniques, the drawings required in the description of the embodiments or the conventional techniques will be briefly introduced below. Apparently, the drawings described below are merely exemplary, and other implementation drawings can be derived from the provided drawings without any constructive efforts by those skilled in the art.

DETAILED DESCRIPTION OF THE EMBODIMENTS

The technical solutions in the embodiments of the present invention will be clearly and completely described below in accordance with the drawings of the embodiments of the present invention. Apparently, the embodiments described below are merely part of the embodiments of the present invention, and are not intended to cover all the embodiments. Any other embodiments achieved by those skilled in the art without any constructive efforts based on the embodiment of the present invention shall fall within the protection scope of the present invention.

Figure 1:
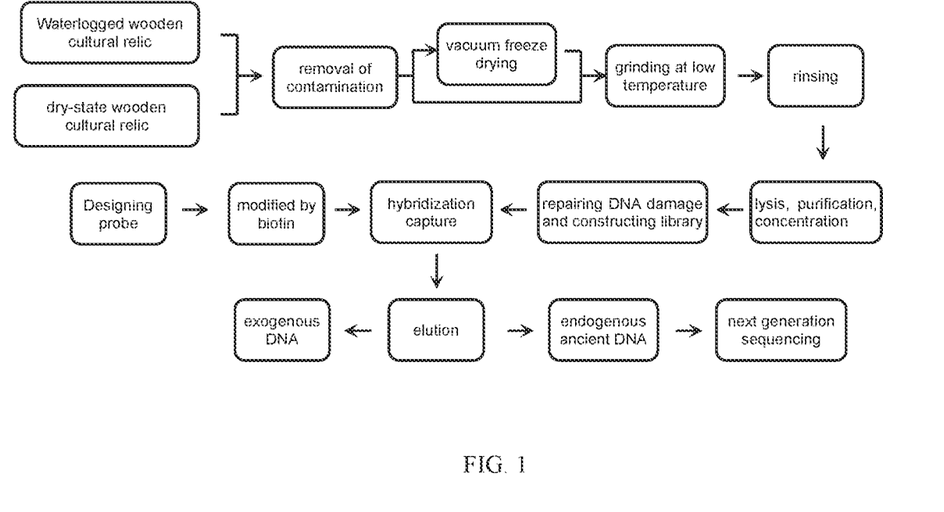
FIG. 1 is a flowchart showing the capture of ancient DNA of wooden cultural relic.
Figure 2:
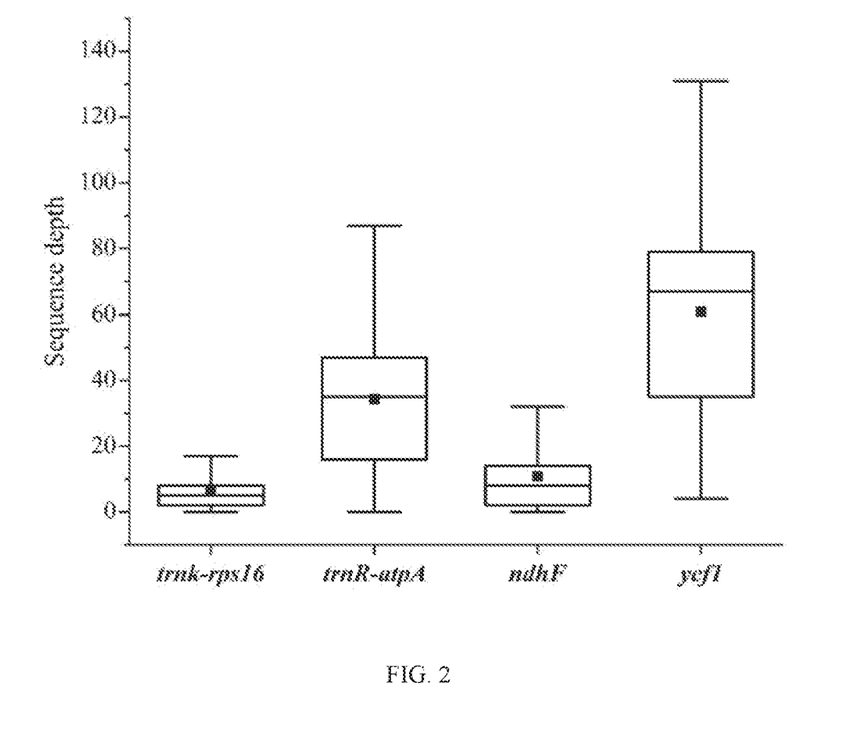
FIG. 2 is a sequencing depth drawing of ancient DNA fragments of waterlogged wooden cultural relic.

As shown in FIG. 1, the present invention provides a method for capturing an ancient DNA of a wooden cultural relic, comprising:

step 100: cutting a wood sample with a volume V from the wooden cultural relic, and removing an exogenous DNA contamination from the wood sample, wherein a method for removing the exogenous DNA contamination of the wood sample sequentially involves with an ultraviolet irradiation, an outer surface removal, a soaking, and a washing, the ultraviolet irradiation is kept for 5-48 h under a radiation of 10-50 W, the outer surface removal is carried out by cutting off an outer surface of the wood sample by 1-4 mm using a sterile scalpel, the soaking is to soak the wood sample in a sodium hypochlorite solution containing a 0.01-0.10% Tween-20 with a mass fraction of 1-5% for 1-10 min, the washing is carried out using a double distilled water for 1-3 times, each time for 1-5 min;

step 200: grinding the wood sample into a powder sample at a low temperature;

step 300: rinsing the powder sample 2-3 times to obtain a rinsed powder sample, wherein a rinsing solution CB for rinsing the powder sample includes a 10-50 mM Tris-HCl at pH=8.0, a 5-20 mM EDTA at pH=8.0, a 5-10% PVP-40, a 5% glycerol, a 5-10% PEG8000, a 300-500 mM sorbitol, and a 50 mM DTT;

step 400: sequentially carrying out a cell lysis, a DNA purification and a concentration on the rinsed powder sample to obtain and collect a sample genomic DNA;

step 500: constructing a DNA library and designing an RNA probe based on the sample genomic DNA, and then hybridizing the RNA probe with the DNA library to form an RNA-DNA complex solution;

step 600: capturing an RNA-DNA complex from the RNA-DNA complex solution using a streptavidin-labeled magnetic bead;

step 700: washing the RNA-DNA complex to obtain a washed RNA-DNA complex, and then dissolving the washed RNA-DNA complex to obtain a target DNA product; and step 800: carrying out a PCR amplification on the target DNA product, and constructing a target DNA library for a high-throughput sequencing.

If the wood sample is a sample from a waterlogged wooden cultural relic, before grinding the wood sample into the powder sample at the low temperature, carrying out a vacuum freeze drying and a dehydration on the wood sample from which the exogenous DNA contamination is removed. In a process of the vacuum freeze drying and the dehydration, the wood sample is pre-frozen in a −20° C. low-temperature refrigerator, and then transported to a freeze dryer to dry under a condition of −40° C., 0.5-2.0 kPa for 36-72 h for the dehydration.

In the above step 200, a method for grinding the wood sample into the powder sample at the low temperature in the step 200 involves with adding a cross-linked polyvinylpyrrolidone powder ½-1 a weight of the wood sample into a grinding tube, and grinding together under a low temperature environment of −196° C., making a powder mesh number not less than 200 mesh.

In the above step 400, the cell lysis involves with preheating a DNA lysis buffer LB to 55° C., adding the DNA lysis buffer LB to the powder sample, oscillating and mixing well to obtain a resulting mixture, and incubating the resulting mixture in a metal bath with an oscillation frequency of 1200 rpm at 50-65° C. for 5-12 h.

In the above step 400, the DNA purification involves with
adding ⅕ volume of a DNA lysis buffer and a chloroform-isoamyl alcohol with a volume ratio of 24:1 to a first centrifuge tube, oscillating and mixing well through a vortex, mixing up and down for 10 min, centrifuging at 8500 g for 15 min to obtain a first supernatant, and transferring the first supernatant to a second centrifuge tube;

adding the chloroform-isoamyl alcohol with the volume ratio of 24:1 in a same volume as that of the first supernatant, oscillating and mixing well through the vortex, centrifuging at 8500 g for 15 min to obtain a second supernatant, and transferring the second supernatant to a freshly sterilized centrifuge tube;

adding a pre-cooled isopropanol in a same volume as a volume of the second supernatant, ⅕ volume of a 3M NaAC (PH=8.0) and 2-10 μl of glycogen, placing a resulting mixture at −20° C. for 1 h, centrifuging at 9000 g for 15 min, and discarding a resulting supernatant;

adding 450 µl of a 70% ethanol solution to wash a precipitate, centrifuging at 8000 g for 10 min, discarding the supernatant, and placing the precipitate on a sterile operating table for drying; and adding the double distilled water to dissolve to obtain the crude DNA extract.

If the crude DNA extract after a primary purification still has a dark color, carrying out a secondary purification on the crude DNA extract using a silicon spin column, wherein a method of the secondary purification involves with adding the crude DNA extract obtained by the primary purification to a binding buffer BB with a volume 10-15 times a volume of the crude DNA extract, and mixing up and down for 2-6 min;

transferring a mixed solution to a silicon spin column combination tube, centrifuging at 2000 g for 10 min, and discarding a filtrate;

centrifuging at 6000 g for 1 min, and drying the silicon spin column;

adding 500-1000 µl of a washing buffer WB, centrifuging at 6000 g for 1 min, washing the silicon spin column, discarding a filtrate, and repeating twice;

centrifuging at 8500 g for 1 min, and drying the silicon spin column; and transferring the silicon spin column to a DNA collection tube, adding 20-50 µl of a release buffer RB, incubating for 5-15 min, centrifuging at a maximum speed for 30 s, and repeating twice, thereby collecting a total of 50 µl of a DNA extract, wherein the binding buffer BB is composed of a 5 M guanidine hydrochloride, a 40% (v/v) isopropanol, a 0.05% Tween-20, and a 90 mM NaAC at pH=5.2;

the washing buffer WB is composed of a 10 mM Tris-HCl at pH=7.5 and a 80% (v/v) ethanol;

the release buffer RB is composed of a 100 mM Tris-HCl at pH=8.0, a 10 mM EDTA at pH=8.0 and a 0.05% Tween-20;

the silicon spin column refers to a combined silicon spin column of a High Pure Extender Assembly of High Pure Viral Nucleic Acid Large Volume Kit (Roche Applied Science).

The DNA lysis buffer LB is composed of a 2% (w/v) CTAB, a 10-50 mM Tris-HCl at pH=8.0, a 50-100 mM NaCl, a 10-20 mM $CaC_2$, a 5-20 mM EDTA at pH=8.0, a 2.5 mM PTB, 4-6% (w/v) PVP-40, a 50-100 mM DTT and a 0.4-0.5 mg/mL proteinase K.

The above step 500 involves with starting a program of a PCR machine, placing a Buffer T1 at 95° C. for 3-5 min, sucking 3-10 µl and then immediately transferring to a first centrifuge tube;

after placing a Buffer T2 at 65° C. for 3-5 min, sucking 5-15 µl and quickly transferring to the first new centrifuge tube;

after placing a Buffer T3 at 65° C. for 1-5 min, sucking 3-10 µl and quickly transferring to the first centrifuge tube;

using a pipette to mix well, sealing a cap of the first centrifuge tube, and hybridizing for 12-48 h, wherein the Buffer T1 is composed of a 1 µg/µL human Cot-1 DNA, a 1 µg/µL salmon sperm DNA, a MYcroarray blocker and a DNA library at a volume ratio of (2-5): (1-4):1:(2-8);

the Buffer T2 is composed of a 0.5 M EDTA, a 20×SSPE buffer, a 50×Denhardt's solution and a 1% SDS at a volume ratio of 1:(10-35): (5-15): (5-12);

the Buffer T3 is composed of a 10 mg/mL yeast tRNA, a RNase inhibitor and a biotinylated RNA probe at a volume ratio of (3-12):1:(0-2.0).

The above step 600 involves with adding a hybridized solution to a centrifuge tube containing a Buffer T4 and a magnetic bead;

incubating the hybridized solution on a rotator at a room temperature for 0.5-2.5 h; and placing a centrifuge tube containing the magnetic bead on a magnetic stand, standing for 3-8 min, and discarding a supernatant, wherein the Buffer T4 is composed of a 1M NaCl, a 10 mM Tris-HCl and a 1 mM EDTA at pH=7.5.

The above step 700 involves with adding 50-300 µL of a Wash Buffer #1 to a second centrifuge tube containing a magnetic bead and mixing through a vortex;

incubating at a room temperature for 5-20 min, and stirring every 3 min;

spinning the second centrifuge tube downward;

placing the second centrifuge tube containing the magnetic bead on a magnetic stand, standing for 1-10 min, and then discarding a supernatant;

adding 50-220 µL of a Wash Buffer #2 to the second centrifuge tube containing the magnetic bead, and mixing through the vortex;

applying a water bath to the magnetic bead and the Wash Buffer #2 at 65° C. for 5-15 min, and stirring once every 2 min;

placing the second centrifuge tube containing the magnetic bead on the magnetic stand, standing for 1-10 min, discarding a supernatant, and repeat twice, wherein the Wash Buffer #1 is composed of a 1×SSC buffer and a 0.05-0.2% SDS buffer, the Wash Buffer #2 is composed of a 0.1×SSC buffer and a 0.05-0.2% SDS buffer, gently removing a residual liquid from the magnetic bead, and eluting with 30-100 µL of a TET buffer to obtain a target DNA solution, wherein the TET buffer is composed of a 10 mM Tris-HCl and a 0.005% Tween 20.

The above step 800 involves with carrying out a Post-PCR amplification on the target DNA solution to construct a DNA library, wherein a reaction system of the PCR amplification is composed of a KAPA Taq HotStart Mix, a Illumina IS5 primer, a Illumina IS6 primer, a DNA and a double distilled water at a volume ratio of (10-50):1:1:(12-25):(3-15);

reaction procedures of the PCR amplification include a pre-denaturation at 94-96° C. for 0.5-10 min, a denaturation at 94-96° C. for 0.1-2 min, an annealing at 40-65° C. for 0.1-2 min, an extension at 72° C. for 0.5-2 min, cycling 20-50 times, and a final extension at 72° C. for 2-15 min.

A method for grinding the wood sample into the powder sample at the low temperature in the step 200 involves with adding a cross-linked polyvinylpyrrolidone powder ½-1 a weight of the wood sample into a grinding tube, and grinding together under a low temperature environment of −196° C., making a powder mesh number not less than 200 mesh.

The cell lysis in the step 400 involves with preheating a DNA lysis buffer LB to 55° C., adding the DNA lysis buffer LB to the powder sample, oscillating and mixing well to obtain a resulting mixture, and incubating the resulting mixture in a metal bath with an oscillation frequency of 1200 rpm at 50-65° C. for 5-12 h.

the DNA purification in the step 400 involves with adding ⅕ volume of a DNA lysis buffer and a chloroform-isoamyl alcohol with a volume ratio of 24:1 to a first centrifuge tube, oscillating and mixing well through a vortex, mixing up and down for 10 min, centrifuging at 8500 g for 15 min to obtain a first supernatant, and transferring the first supernatant to a second centrifuge tube;

adding the chloroform-isoamyl alcohol with the volume ratio of 24:1 in a same volume as that of the first supernatant, oscillating and mixing well through the vortex, centrifuging at 8500 g for 15 min to obtain a second supernatant, and transferring the second supernatant to a freshly sterilized centrifuge tube;

adding a pre-cooled isopropanol in a same volume as a volume of the second supernatant, ⅕ volume of a 3M NaAC (PH=8.0), and 2-10 μl of glycogen, placing a resulting mixture at −20° C. for 1 h, centrifuging at 9000 g for 15 min, and discarding a resulting supernatant;

adding 450 μl of a 70% ethanol solution to wash a precipitate, centrifuging at 8000 g for 10 min, discarding the supernatant, and placing the precipitate on a sterile operating table for drying; and adding the double distilled water to dissolve to obtain a DNA crude extract.

If a DNA crude extract after a primary purification still has a dark color, carrying out a secondary purification on the DNA crude extract using a silicon spin column, wherein a method of the secondary purification involves with adding the DNA crude extract obtained by the primary purification to a binding buffer BB with a volume 10-15 times a volume of the DNA crude extract, and mixing up and down for 2-6 min;

transferring a mixed solution to a silicon spin column combination tube, centrifuging at 2000 g for 10 min, and discarding a filtrate;

centrifuging at 6000 g for 1 min, and drying the silicon spin column;

transferring the silicon spin column to a DNA collection tube, adding 20-50 μl of a release buffer RB, incubating for 5-15 min, centrifuging at a maximum speed for 30 s, and repeating twice, thereby collecting a total of 50 μl of a DNA extract, wherein the binding buffer BB is composed of a 5 M guanidine hydrochloride, a 40% (v/v) isopropanol, a 0.05% Tween-20, and a 90 mM NaAC at pH=5.2;

the washing buffer WB is composed of a 10 mM Tris-HCl at pH=7.5 and a 80% (v/v) ethanol;

the release buffer RB is composed of a 100 mM Tris-HCl at pH=8.0, a 10 mM EDTA at pH=8.0, and a 0.05% Tween-20;

the silicon spin column refers to a combined silicon spin column of a High Pure Extender Assembly of High Pure Viral Nucleic Acid Large Volume Kit (Roche Applied Science).

the step 500 involves with starting a program of a PCR machine, placing a Buffer T1 at 95° C. for 3-5 min, sucking 3-10 μl and then immediately transferring to a first centrifuge tube;

after placing a Buffer T2 at 65° C. for 3-5 min, sucking 5-15 μl and quickly transferring to the first centrifuge tube;

after placing a Buffer T3 at 65° C. for 1-5 min, sucking 3-10 μl and quickly transferring to the first centrifuge tube;

using a pipette to mix well, sealing a cap of the first centrifuge tube, and hybridizing for 12-48 h, wherein the Buffer T1 is composed of a 1 μg/μL human Cot-1 DNA, a 1 μg/μL salmon sperm DNA, a MYcroarray blocker, and the DNA library at a volume ratio of (2-5):(1-4):1:(2-8);

the Buffer T2 is composed of a 0.5 M EDTA, a 20×SSPE buffer, a 50×Denhardt's solution, and a 1% SDS at a volume ratio of 1:(10-35):(5-15):(5-12);

the Buffer T3 is composed of a 10 mg/mL yeast tRNA, a RNase inhibitor, and a biotinylated RNA probe at a volume ratio of (3-12):1:(0-2.0).

The step 600 involves with adding a hybridized solution to a centrifuge tube containing a Buffer T4 and a magnetic bead;

incubating the hybridized solution on a rotator at a room temperature for 0.5-2.5 h; and placing a centrifuge tube containing the magnetic bead on a magnetic stand, standing for 3-8 min, and discarding a supernatant, wherein the Buffer T4 is composed of a 1M NaCl, a 10 mM Tris-HCl, and 1 mM EDTA at pH=7.5.

The present invention provides the method for capturing ancient DNA of wooden cultural relic, which includes sample pretreatment, wood cell lysis, ancient DNA genome enrichment, hybrid capture, etc. By removing the exogenous DNA contamination existing at the inner part and outer surface of the sample, and carrying out vacuum freeze drying and dehydration, sample grinding, rinsing and other treatment measures during the pretreatment process of the sample, the present invention can solve the problems that the endogenous ancient DNA is difficult to capture through conventional polymerase chain reaction (PCR reaction), or even impossible to be amplified, which breaks through the technical bottleneck of the conventional wood DNA extraction and PCR amplification methods.

The present invention focuses on precise capture of the ancient DNA of the wood cells of the wood cultural relic, not only breaks through the problem that effective acquisition of DNA of the wood cultural relic is difficult to realize by a conventional wood DNA extraction method, but also provides possibility for analysis and utilization of the ancient DNA with typical characteristics such as serious exogenous contamination, low DNA content, high degradation, extensive damage and the like. The method can be used in the fields of identification, protection and restoration of dry-state and waterlogged wood cultural relic tree species, and is high in practicability.

Since free moisture is a necessary condition for the hydrolysis and oxidation reactions of the ancient DNA, the moisture is an important factor leading to the degradation of ancient DNA. The hydrolysis reaction will break the DNA phosphodiester bond or cause deamination reaction, as well as destroy the hydrogen bond force of the double strand of DNA molecule; and the oxidation reaction will lead to the loss or change of the base. Therefore, compared with materials such as dry-state wooden components of ancient buildings on the ground, the DNA preservation status of waterlogged archaeological wood is worse, which seriously restricts the tree species identification and subsequent data analysis thereof.

Therefore, for the sample of waterlogged wooden cultural relic, the vacuum freeze drying and dehydration method is used to remove the moisture from waterlogged archaeological wood, and reduce the viscosity of sample to improve the grinding effect of wood powder; and meanwhile, the moisture is removed from the sample on the premise of avoiding further damage to the ancient DNA through the temperature control, which reduces the substantial quality difference caused by the different water content of the sample, and ensures the stability of the sample extraction amount.

In addition, the present invention introduces the rinsing method to rinse the unearthed archaeological wood, so as to eliminate the interference of humus and other substances on the extraction of ancient DNA.

The present invention adopts the combined silicon spin column of High Pure Extender Assembly of High Pure Viral Nucleic Acid Large Volume Kit (Roche Applied Science Qiagen) to complete the suction of ancient DNA in all extracts at once, which not only fully removes impurities such as polyphenols and polysaccharides, but also reduces the possibility of exogenous contamination caused by human operation as much as possible at the same time.

In summary, the present invention provides a new approach for accurate identification of wood species of wood cultural relic.

The above solutions will be described below by taking the waterlogged wooden cultural relic as an example in accompany with specific embodiments.

EMBODIMENTS

1. DNA extraction of unearthed waterlogged wood: the waterlogged wood cultural relic is unearthed from an archaeological site in southern of China. The wood sample with a volume of 3.3×3 cm is cut off from the wooden cultural relic, a part for wood anatomy detection, and the other part for ancient DNA extraction. After the wood morphology identification, it is determined to be *Quercus* wood.

Before the DNA extraction operation, first carrying out an exogenous contamination removal operation on the wood sample, which involves with an ultraviolet irradiation for 24 h under the radiation of 50 W, cutting off an outer surface of the wood sample by 3 mm using a sterile scalpel, soaking the sample in a sodium hypochlorite solution containing a 0.10% Tween-20 with a mass fraction of 5% for 10 min, and washing using a double distilled water twice, each time for 3 min.

Carrying out a vacuum freeze drying and a dehydration on the wood sample, which involves with first pre-freezing the wood sample in a −20° C. low-temperature refrigerator, and then transporting to a freeze dryer to dry under a condition of −40° C., 2.0 kPa for 36 h for a dehydration.

Freezing-grinding into a wood powder, which involves with adding a cross-linked polyvinylpyrrolidone powder that is 0.5 times a weight of the wood sample into a grinding tube, and grinding together under a low temperature environment of −196° C., making a powder mesh number not less than 200 mesh.

Using a rinsing solution CB (composed of a 25 mM Tris-HCl at pH=8.0, a 20 mM EDTA at pH=8.0, a 6% PVP-40, a 5% glycerol, a 5% PEG8000, a 350 mM sorbitol and a 50 mM DTT) for rinsing the wood powder, so as to effectively remove humic acid and metabolites.

Adding a DNA lysis buffer LB (composed of a 2% (w/w) CTAB, a 20 mM Tris-HCl at pH=8.0, a 75 mM NaCl, a 10 mM $CaCl_2$, a 20 mM EDTA at pH=8.0, a 2.5 mM PTB, a 6% (w/v) PVP-40, a 75 mM DTT and a 0.4 mg/mL proteinase K) to the wood powder, oscillating and mixing well to obtain a resulting mixture, and incubating the resulting mixture in a metal bath with an oscillation frequency of 1200 rpm at 55° C. for 12 h.

In a process of DNA purification, adding ⅕ volume of a DNA lysis buffer and a chloroform-isoamyl alcohol with a volume ratio of 24:1 to a first centrifuge tube after cell lysis, oscillating and mixing well through a vortex, mixing up and down for 10 min, centrifuging at 8500 g for 15 min to obtain a first supernatant, and transferring the first supernatant to a second centrifuge tube.

Adding the chloroform-isoamyl alcohol (24:1, v/v) in the same volume as that of the first supernatant, oscillating and mixing well through a vortex, centrifuging at 8500 g for 15 min to obtain a second supernatant, and transferring the second supernatant to a freshly sterilized centrifuge tube.

Adding pre-cooled isopropanol in a same volume as a volume of the second supernatant, ⅕ volume of a 3M NaAC (PH=8.0) and a 10 μl of glycogen, placing a resulting mixture at −20° C. for 1 h, centrifuging at 9000 g for 15 min, and discarding a resulting supernatant; adding 450 μl of a 70% ethanol solution to wash a precipitate, centrifuging at 8000 g for 10 min, discarding the supernatant, and placing the precipitate on a sterile operating table to dry; and adding the double distilled water to dissolve to the crude DNA extract.

If the crude DNA extract after a primary purification still has a dark color, carrying out a secondary purification on the crude DNA extract using a silicon spin column.

A method of the secondary purification involves with adding the crude DNA extract obtained by the primary purification to a binding buffer BB (composed of a 5 M guanidine hydrochloride, a 40% (v/v) isopropanol, a 0.05% Tween-20, and a 90 mM NaAC at pH=5.2) with a volume 13 times a volume of the crude DNA extract, and mixing up and down for 5 min; transferring a mixed solution to a silicon spin column combination tube, centrifuging at 2000 g for 10 min, and discarding a filtrate; centrifuging at 6000 g for 1 min, and drying the silicon spin column; adding 700 μl of a washing buffer WB (composed of a 10 mM Tris-HCl at pH=7.5 and a 80% (v/v) ethanol), centrifuging at 6000 g for 1 min, washing the silicon spin column, discarding a filtrate, and repeating twice; centrifuging at 8500 g for 1 min, and drying the silicon spin column; and transferring the silicon spin column to a DNA collection tube, adding 25 μl of a release buffer RB (composed of a 100 mM Tris-HCl at pH=8.0, a 10 mM EDTA at pH=8.0 and a 0.05% Tween-20), incubating for 10 min, centrifuging at the maximum speed for 30 s, and repeating twice, obtaining a total of 50 μl of a DNA extract.

2. Selection of High-Resolution DNA Fragments for Identifying DNA of Wooden Cultural Relic Carrying out a chloroplast genome comparison on 24 *Quercus* species based on the Pi value by using DNAsp software, so as to determine that four DNA fragments including tmk-rps16, tmR-atpA, ndhF and ycf1 are high-resolution DNA barcodes (doi.org/10.3390/ijms20235940).

3. Hybrid Capture of DNA of Wooden Cultural Relic

Designing an RNA probe based on four DNA fragments including trnk-rps16, trnR-atpA, ndhF and ycf1 in *Quercus acutissima* (accession number MH607377) published by GenBank as references.

Starting a program of a PCR machine, placing a Buffer T1 (composed of a 1 μg/μL human Cot-1 DNA, a 1 μg/μL salmon sperm DNA, a MYcroarray blocker and a DNA library) at 95° C. for 3-5 min, sucking 8 μl and then immediately transferring it to a first centrifuge tube; after placing a Buffer T2 (composed of a 0.5 M EDTA, a 20×SSPE buffer, a 50×Denhardt's solution and a 1% SDS) at 65° C. for 3-5 min, sucking 10 μl and then quickly transferring to the first centrifuge tube; after placing a Buffer T3 (composed of a 10 mg/mL yeast tRNA, a RNase inhibitor and a biotinylated RNA probe) at 65° C. for 5 min, sucking 7 μl and then quickly transferring to the first centrifuge tube; using a pipette to mix well, sealing a cap of the first centrifuge tube, and hybridizing for 48 h.

Adding a hybridized solution to a centrifuge tube containing a Buffer T4 (composed of a 1M NaCl, a 10 mM Tris-HCl and a 1 mM EDTA at pH=7.5) and a magnetic bead; incubating the hybridized solution on a rotator at a room temperature for 0.5-2.5 h; and placing the magnetic bead on a magnetic stand, standing for 3-8 min, and discarding a supernatant.

Adding 150 μL of a Wash Buffer #1 (composed of a 1×SSC buffer and a 0.1% SDS) to the magnetic bead and mixing through a vortex; incubating at a room temperature for 5-20 min, and stirring every 3 min; spinning the second centrifuge tube downward; placing the magnetic bead on the magnetic stand, standing for 5 min, and then discarding a supernatant; adding 180 μL of a Wash Buffer #2 (composed of a 0.1×SSC buffer and a 0.05-0.2% SDS) to the magnetic bead, and mixing through the vortex; applying a water bath to the magnetic bead and the Wash Buffer #2 at 65° C. for 5-15 min, and stirring once every 2 min; and placing the magnetic bead on the magnetic stand, standing for 1-10 min, discarding a supernatant, and repeat the steps twice.

Gently removing a residual liquid from the magnetic bead, eluting with 80 μL of a TET buffer (composed of a 10 mM Tris-HCl and a 0.005% Tween 20; and a reaction system for PCR amplification is composed of a KAPA Taq HotStart Mix, a Illumina IS5 primer, a Illumina IS6 primer, a DNA and a double distilled water), and carrying out a Post-PCR amplification to construct a library.

The reaction procedures of a PCR amplification include a pre-denaturation at 94-96° C. for 0.5-10 min, a denaturation at 94-96° C. for 0.1-2 min, an annealing at 40-65° C. for 0.1-2 min, an extension at 72° C. for 0.5-2 min, cycling 20-50 times, and a final extension at 72° C. for 2-15 min.

4. Species Identification Using DNA of Wooden Cultural Relic

Carrying out high-throughput sequencing on the enriched DNA library based on the Illumina platform. Using AdapterRemoval2 to perform a quality control, a joint removal and a filtering on sequencing reads, and evaluating the authenticity of the ancient DNA based on mapDamage 2.0; comparing the sequence after the quality control with the reference the genome of similar species using BWA-aln algorithm (mapping), and discarding reads of which the alignment quality is lower than 25 and the PCR duplicates; using a sam2consensus, an EAGER and an ANGSD to generate consistent ancient DNA sequences.

Carrying out species identification in the GenBank data using a BLAST method. Finally, the sample is identified as *Quercus acutissima* through comprehensive comparison of the four barcodes.

TABLE 1

Identification of wood species based on BLAST method

| sequence | species | representative registration number | highest similarity |
| --- | --- | --- | --- |
| trnk-rps16 | *Quercus acutissima* | MH607377 | 100% |
| | *Quercus variablilis* | MK105466 | |
| | *Quercus chenii* | MF593894 | |

TABLE 1-continued

Identification of wood species based on BLAST method

| sequence | species | representative registration number | highest similarity |
| --- | --- | --- | --- |
| trnR-atpA | *Quercus* spp. | — | 100% |
| ndhF | *Quercus acutissima* | MH607377 | 99.77% |
| ycfl | *Quercus* spp. | — | 100% |

The above embodiments are merely exemplary embodiments of the present application, and are not intended to limit the present application. The protection scope of the present application is defined by the claims. Any modifications or equivalent replacements made by those skilled in the art within the spirit and protection scope of the present application shall also be deemed to fall within the protection scope of the present application.

What is claimed is:

1. A method for capturing an ancient DNA of a wooden cultural relic, comprising:

step 100: cutting a wood sample with a volume V from the wooden cultural relic, and removing an exogenous DNA contamination from the wood sample, wherein a method for removing the exogenous DNA contamination of the wood sample sequentially comprises an ultraviolet irradiation, an outer surface removal, a soaking, and a washing, the ultraviolet irradiation is kept for 5-48 h under a radiation of 10-50 W, the outer surface removal is carried out by cutting off an outer surface of the wood sample by 1-4 mm using a sterile scalpel, the soaking is to soak the wood sample in a sodium hypochlorite solution containing 0.01-0.10% Tween-20 with a mass fraction of 1-5% for 1-10 min, the washing is carried out using a double distilled water for 1-3 times, each time for 1-5 min;

step 200: grinding the wood sample into a powder sample at a low temperature;

step 300: rinsing the powder sample 2-3 times to obtain a rinsed powder sample, wherein a rinsing solution CB for rinsing the powder sample includes 10-50 mM Tris-HCl at pH=8.0, 5-20 mM EDTA at pH=8.0, 5-10% PVP-40, 5% glycerol, 5-10% PEG8000, 300-500 mM sorbitol, and 50 mM DTT;

step 400: sequentially carrying out a cell lysis, a DNA purification, and a concentration on the rinsed powder sample to obtain and collect a sample genomic DNA;

step 500: constructing a DNA library and designing an RNA probe based on the sample genomic DNA, and then hybridizing the RNA probe with the DNA library to form an RNA-DNA complex solution;

step 600: capturing an RNA-DNA complex from the RNA-DNA complex solution using a streptavidin-labeled magnetic bead;

step 700: washing the RNA-DNA complex to obtain a washed RNA-DNA complex, and then dissolving the washed RNA-DNA complex to obtain a target DNA product; and step 800: carrying out a PCR amplification on the target DNA product, and constructing a target DNA library for a high-throughput sequencing.

2. The method for capturing the ancient DNA of the wooden cultural relic according to claim 1, wherein
if the wood sample is a sample from a waterlogged wooden cultural relic, before grinding the wood sample into the powder sample at the low temperature, carrying out a vacuum freeze drying and a dehydration on the wood sample from which the exogenous DNA contamination is removed.

3. The method for capturing the ancient DNA of the wooden cultural relic according to claim 2, wherein
in a process of the vacuum freeze drying and the dehydration, the wood sample is pre-frozen in a −20° C. low-temperature refrigerator, and then transported to a freeze dryer to dry under a condition of −40° C., 0.5-2.0 kPa for 36-72 h for the dehydration.

4. The method for capturing the ancient DNA of the wooden cultural relic according to claim 1, wherein
a method for grinding the wood sample into the powder sample at the low temperature in the step 200 comprises:
adding a cross-linked polyvinylpyrrolidone powder ½-1 a weight of the wood sample into a grinding tube, and grinding together under a low temperature environment of −196° C., making a powder mesh number not less than 200 mesh.

5. The method for capturing the ancient DNA of the wooden cultural relic according to claim 1, wherein
the cell lysis in the step 400 comprises preheating a DNA lysis buffer LB to 55° C., adding the DNA lysis buffer LB to the powder sample, oscillating and mixing well to obtain a resulting mixture, and incubating the resulting mixture in a metal bath with an oscillation frequency of 1200 rpm at 50-65° C. for 5-12 h.

6. The method for capturing the ancient DNA of the wooden cultural relic according to claim 1, wherein
the DNA purification in the step 400 comprises:
adding ⅓ volume of a DNA lysis buffer and a chloroform-isoamyl alcohol with a volume ratio of 24:1 to a first centrifuge tube, oscillating and mixing well through a vortex, mixing up and down for 10 min, centrifuging at 8500 g for 15 min to obtain a first supernatant, and transferring the first supernatant to a second centrifuge tube;
adding the chloroform-isoamyl alcohol with the volume ratio of 24:1 in a same volume as that of the first supernatant, oscillating and mixing well through the vortex, centrifuging at 8500 g for 15 min to obtain a second supernatant, and transferring the second supernatant to a freshly sterilized centrifuge tube;
adding a pre-cooled isopropanol in a same volume as a volume of the second supernatant, ⅕ volume of 3M NaAC (PH=8.0), and 2-10 µl of glycogen, placing a resulting mixture at −20° C. for 1 h, centrifuging at 9000 g for 15 min, and discarding a resulting supernatant;
adding 450 µl of a 70% ethanol solution to wash a precipitate, centrifuging at 8000 g for 10 min, discarding the supernatant, and placing the precipitate on a sterile operating table for drying; and
adding the double distilled water to dissolve to obtain a crude DNA extract.

7. The method for capturing the ancient DNA of the wooden cultural relic according to claim 1, wherein
if a crude DNA extract after a primary purification still has a dark color, carrying out a secondary purification on the crude DNA extract using a silicon spin column, wherein a method of the secondary purification comprises:
adding the crude DNA extract obtained by the primary purification to a binding buffer BB with a volume 10-15 times a volume of the crude DNA extract, and mixing up and down for 2-6 min;
transferring a mixed solution to a silicon spin column combination tube, centrifuging at 2000 g for 10 min, and discarding a filtrate;
centrifuging at 6000 g for 1 min, and drying the silicon spin column;
adding 500-1000 µl of a washing buffer WB, centrifuging at 6000 g for 1 min, washing the silicon spin column, discarding a filtrate, and repeating twice;
centrifuging at 8500 g for 1 min, and drying the silicon spin column; and
transferring the silicon spin column to a DNA collection tube, adding 20-50 µl of a release buffer RB, incubating for 5-15 min, centrifuging at a maximum speed for 30 s, and repeating twice, thereby collecting a total of 50 µl of a DNA extract, wherein
the binding buffer BB is composed of 5 M guanidine hydrochloride, 40% (v/v) isopropanol, 0.05% Tween-20, and 90 mM NaAC at pH=5.2;
the washing buffer WB is composed of 10 mM Tris-HCl at pH=7.5 and 80% (v/v) ethanol;
the release buffer RB is composed of 100 mM Tris-HCl at pH=8.0, 10 mM EDTA at pH=8.0, and 0.05% Tween-20;
the silicon spin column refers to a combined silicon spin column of a High Pure Extender Assembly of High Pure Viral Nucleic Acid Large Volume Kit (Roche Applied Science).

8. The method for capturing the ancient DNA of the wooden cultural relic according to claim 5, wherein
the DNA lysis buffer LB is composed of 2% (w/v) CTAB, 10-50 mM Tris-HCl at pH=8.0, 50-100 mM NaCl, 10-20 mM CaCl$_2$, 5-20 mM EDTA at pH=8.0, 2.5 mM PTB, 4-6% (w/v) PVP-40, 50-100 mM DTT, and 0.4-0.5 mg/mL proteinase K.

9. The method for capturing the ancient DNA of the wooden cultural relic according to claim 1, wherein
the step 500 comprises:
starting a program of a PCR machine, placing a Buffer T1 at 95° C. for 3-5 min, sucking 3-10 µl and then immediately transferring to a first centrifuge tube;
after placing a Buffer T2 at 65° C. for 3-5 min, sucking 5-15 µl and quickly transferring to the first centrifuge tube;
after placing a Buffer T3 at 65° C. for 1-5 min, sucking 3-10 µl and quickly transferring to the first centrifuge tube;
using a pipette to mix well, sealing a cap of the first centrifuge tube, and hybridizing for 12-48 h, wherein
the Buffer T1 is composed of 1 µg/µL human Cot-1 DNA, 1 µg/µL salmon sperm DNA, a MYcroarray blocker, and the DNA library at a volume ratio of (2-5):(1-4):1:(2-8);
the Buffer T2 is composed of 0.5 M EDTA, a 20×SSPE buffer, 50×Denhardt's solution, and 1% SDS at a volume ratio of 1:(10-35):(5-15):(5-12);
the Buffer T3 is composed of 10 mg/mL yeast tRNA, a RNase inhibitor, and a biotinylated RNA probe at a volume ratio of (3-12):1:(0-2.0).

10. The method for capturing the ancient DNA of the wooden cultural relic according to claim 1, wherein
the step 600 comprises:
adding a hybridized solution to a centrifuge tube containing a Buffer T4 and a magnetic bead;
incubating the hybridized solution on a rotator at a room temperature for 0.5-2.5 h; and
placing a centrifuge tube containing the magnetic bead on a magnetic stand, standing for 3-8 min, and discarding a supernatant, wherein
the Buffer T4 is composed of 1 M NaCl, 10 mM Tris-HCl, and 1 mM EDTA at pH=7.5.

11. The method for capturing the ancient DNA of the wooden cultural relic according to claim 9, wherein
the step 700 comprises:
adding 50-300 μL of a Wash Buffer #1 to a second centrifuge tube containing a magnetic bead and mixing through a vortex;
incubating at a room temperature for 5-20 min, and stirring every 3 min;
spinning the second centrifuge tube downward;
placing the second centrifuge tube containing the magnetic bead on a magnetic stand, standing for 1-10 min, and then discarding a supernatant;
adding 50-220 μL of a Wash Buffer #2 to the second centrifuge tube containing the magnetic bead, and mixing through the vortex;
applying a water bath to the magnetic bead and the Wash Buffer #2 at 65° C. for 5-15 min, and stirring once every 2 min;
placing the second centrifuge tube containing the magnetic bead on the magnetic stand, standing for 1-10 min, discarding a supernatant, and repeat twice, wherein
the Wash Buffer #1 is composed of a 1×SSC buffer and a 0.05-0.2% SDS buffer,
the Wash Buffer #2 is composed of a 0.1×SSC buffer and a 0.05-0.2% SDS buffer;
gently removing a residual liquid from the magnetic bead, and eluting with 30-100 μL of a TET buffer to obtain a target DNA solution, wherein
the TET buffer is composed of 10 mM Tris-HCl and 0.005% Tween 20.

12. The method for capturing the ancient DNA of the wooden cultural relic according to claim 11, wherein
the step 800 comprises:
carrying out a Post-PCR amplification on the target DNA solution to construct the DNA library, wherein
a reaction system of the PCR amplification is composed of a KAPA Taq HotStart Mix, a Illumina IS5 primer, a Illumina IS6 primer, a DNA, and the double distilled water at a volume ratio of (10-50):1:1:(12-25):(3-15);
reaction procedures of the PCR amplification include a pre-denaturation at 94-96° C. for 0.5-10 min, a denaturation at 94-96° C. for 0.1-2 min, an annealing at 40-65° C. for 0.1-2 min, an extension at 72° C. for 0.5-2 min, cycling 20-50 times, and a final extension at 72° C. for 2-15 min.

13. The method for capturing the ancient DNA of the wooden cultural relic according to claim 2, wherein
a method for grinding the wood sample into the powder sample at the low temperature in the step 200 comprises:
adding a cross-linked polyvinylpyrrolidone powder ½-1 a weight of the wood sample into a grinding tube, and grinding together under a low temperature environment of −196° C., making a powder mesh number not less than 200 mesh.

14. The method for capturing the ancient DNA of the wooden cultural relic according to claim 2, wherein
the cell lysis in the step 400 comprises preheating a DNA lysis buffer LB to 55° C., adding the DNA lysis buffer LB to the powder sample, oscillating and mixing well to obtain a resulting mixture, and incubating the resulting mixture in a metal bath with an oscillation frequency of 1200 rpm at 50-65° C. for 5-12 h.

15. The method for capturing the ancient DNA of the wooden cultural relic according to claim 2, wherein
the DNA purification in the step 400 comprises:
adding ⅕ volume of a DNA lysis buffer and a chloroform-isoamyl alcohol with a volume ratio of 24:1 to a first centrifuge tube, oscillating and mixing well through a vortex, mixing up and down for 10 min, centrifuging at 8500 g for 15 min to obtain a first supernatant, and transferring the first supernatant to a second centrifuge tube;
adding the chloroform-isoamyl alcohol with the volume ratio of 24:1 in a same volume as that of the first supernatant, oscillating and mixing well through the vortex, centrifuging at 8500 g for 15 min to obtain a second supernatant, and transferring the second supernatant to a freshly sterilized centrifuge tube;
adding a pre-cooled isopropanol in a same volume as a volume of the second supernatant, ⅕ volume of 3M NaAC (PH=8.0), and 2-10 μl of glycogen, placing a resulting mixture at −20° C. for 1 h, centrifuging at 9000 g for 15 min, and discarding a resulting supernatant;
adding 450 μl of a 70% ethanol solution to wash a precipitate, centrifuging at 8000 g for 10 min, discarding the supernatant, and placing the precipitate on a sterile operating table for drying; and
adding the double distilled water to dissolve to obtain a crude DNA extract.

16. The method for capturing the ancient DNA of the wooden cultural relic according to claim 2, wherein
if a crude DNA extract after a primary purification still has a dark color, carrying out a secondary purification on the crude DNA extract using a silicon spin column, wherein a method of the secondary purification comprises:
adding the crude DNA extract obtained by the primary purification to a binding buffer BB with a volume 10-15 times a volume of the crude DNA extract, and mixing up and down for 2-6 min;
transferring a mixed solution to a silicon spin column combination tube, centrifuging at 2000 g for 10 min, and discarding a filtrate;
centrifuging at 6000 g for 1 min, and drying the silicon spin column;
adding 500-1000 μl of a washing buffer WB, centrifuging at 6000 g for 1 min, washing the silicon spin column, discarding a filtrate, and repeating twice;
centrifuging at 8500 g for 1 min, and drying the silicon spin column; and
transferring the silicon spin column to a DNA collection tube, adding 20-50 μl of a release buffer RB, incubating for 5-15 min, centrifuging at a maximum speed for 30 s, and repeating twice, thereby collecting a total of 50 μl of a DNA extract, wherein the binding buffer BB is composed of 5 M guanidine hydrochloride, 40% (v/v) isopropanol, 0.05% Tween-20, and 90 mM NaAC at pH=5.2;

the washing buffer WB is composed of 10 mM Tris-HCl at pH=7.5 and 80% (v/v) ethanol;

the release buffer RB is composed of 100 mM Tris-HCl at pH=8.0, 10 mM EDTA at pH=8.0, and 0.05% Tween-20;

the silicon spin column refers to a combined silicon spin column of a High Pure Extender Assembly of High Pure Viral Nucleic Acid Large Volume Kit (Roche Applied Science).

17. The method for capturing the ancient DNA of the wooden cultural relic according to claim 2, wherein the step 500 comprises:

starting a program of a PCR machine, placing a Buffer T1 at 95° C. for 3-5 min, sucking 3-10 μl and then immediately transferring to a first centrifuge tube;

after placing a Buffer T2 at 65° C. for 3-5 min, sucking 5-15 μl and quickly transferring to the first centrifuge tube;

after placing a Buffer T3 at 65° C. for 1-5 min, sucking 3-10 μl and quickly transferring to the first centrifuge tube;

using a pipette to mix well, sealing a cap of the first centrifuge tube, and hybridizing for 12-48 h, wherein the Buffer T1 is composed of 1 μg/μL human Cot-1 DNA, 1 μg/μL salmon sperm DNA, a MYcroarray blocker, and the DNA library at a volume ratio of (2-5):(1-4):1:(2-8);

the Buffer T2 is composed of 0.5 M EDTA, a 20×SSPE buffer, a 50×Denhardt's solution, and 1% SDS at a volume ratio of 1:(10-35):(5-15):(5-12);

the Buffer T3 is composed of 10 mg/mL yeast tRNA, a RNase inhibitor, and a biotinylated RNA probe at a volume ratio of (3-12):1:(0-2.0).

18. The method for capturing the ancient DNA of the wooden cultural relic according to claim 2, wherein the step 600 comprises:

adding a hybridized solution to a centrifuge tube containing a Buffer T4 and a magnetic bead;

incubating the hybridized solution on a rotator at a room temperature for 0.5-2.5 h; and placing a centrifuge tube containing the magnetic bead on a magnetic stand, standing for 3-8 min, and discarding a supernatant, wherein the Buffer T4 is composed of 1M NaCl, 10 mM Tris-HCl, and 1 mM EDTA at pH=7.5.

* * * * *